United States Patent [19]

Kato

[11] Patent Number: 5,877,406

[45] Date of Patent: Mar. 2, 1999

[54] $NO_X$ SENSOR AND METHOD OF MEASURING $NO_X$

[75] Inventor: Nobuhide Kato, Ama-gun, Japan

[73] Assignee: NGK Insulators, Ltd., Japan

[21] Appl. No.: 80,391

[22] Filed: May 18, 1998

Related U.S. Application Data

[63] Continuation of Ser. No. 732,599, Oct. 15, 1996.

[30] Foreign Application Priority Data

Oct. 20, 1995 [JP] Japan ...................... 7-272458

[51] Int. Cl.$^6$ .................... G01N 27/419; G01N 27/46
[52] U.S. Cl. ................................... 73/23.31
[58] Field of Search ........................ 73/23.31, 23.32, 73/31.05, 31.06, 116, 117.2, 117.3, 118.1, 118.2; 701/103, 109

[56] References Cited

U.S. PATENT DOCUMENTS

| | | | |
|---|---|---|---|
| 5,034,112 | 7/1991 | Murase et al. | 204/406 |
| 5,145,566 | 9/1992 | Logothetis et al. | 204/153.18 |
| 5,217,588 | 6/1993 | Wang et al. | 204/153.1 |
| 5,397,442 | 3/1995 | Wachsman | 73/23.31 |
| 5,476,001 | 12/1995 | Hoetzel et al. | 73/23.31 |
| 5,493,896 | 2/1996 | Riegel | 73/23.31 |
| 5,507,174 | 4/1996 | Friese et al. | 73/23.32 |

FOREIGN PATENT DOCUMENTS

| | | |
|---|---|---|
| 0 257 842 | 3/1988 | European Pat. Off. . |
| 4359144 A | of 1993 | European Pat. Off. . |
| 0 678 740 A1 | 10/1995 | European Pat. Off. . |
| 0 731 351 A2 | 9/1996 | European Pat. Off. . |
| 61-183099 | 2/1988 | Japan . |
| 6-72861 | 9/1994 | Japan . |
| 8-29387 | 2/1996 | Japan . |
| WO 95/30146 | 11/1995 | WIPO . |

OTHER PUBLICATIONS

Patent Abstract of Japan, vol. 017, No. 231, May 11, 1993 and JP –A–04 359144 (Mitsubishi motors Corp.), Dec. 11, 1992, abstract.

*Primary Examiner*—George Dombroske
*Attorney, Agent, or Firm*—Parkhurst & Wendel, L.L.P.

[57] ABSTRACT

Disclosed is a NOx sensor and a method of measuring NOx capable of obtaining a large change in signal to measure a concentration of low concentration NOx in a measurement gas continuously and accurately with good response over a long period of time. A NOx sensor comprises a first internal space into which the measurement gas is introduced through a first diffusion rate-determining passage, a second internal space arranged with a NOx-reducing catalyst, into which an atmosphere is introduced through a second diffusion rate-determining passage, an electrochemical pumping cell for controlling a partial pressure of oxygen in the internal space by using a first oxygen ion-conductive solid electrolyte and electro-chemical cells provided in contact therewith, a partial oxygen pressure-detecting means for detecting the partial pressure of oxygen in the internal space by using the first oxygen ion-conductive solid electrolyte and electro-chemical cells provided in contact therewith, a first electro-chemical sensor cell for outputting an electromotive force corresponding to the partial pressure of oxygen in the internal space, and a voltage-detecting means for detecting the electromotive force outputted from the first electro-chemical sensor cell. The NOx concentration is determined from a value of the electromotive force of the first electro-chemical sensor cell detected by the voltage-detecting means.

4 Claims, 7 Drawing Sheets

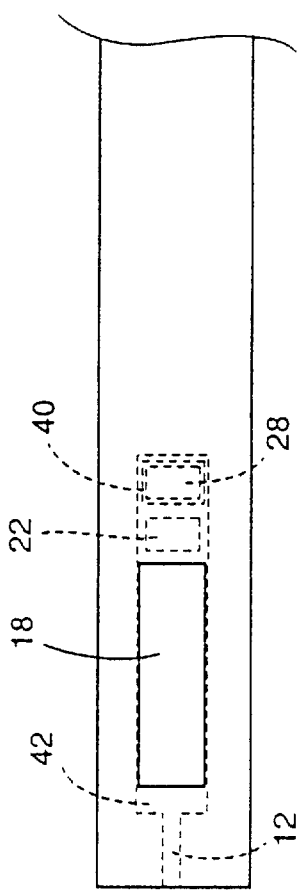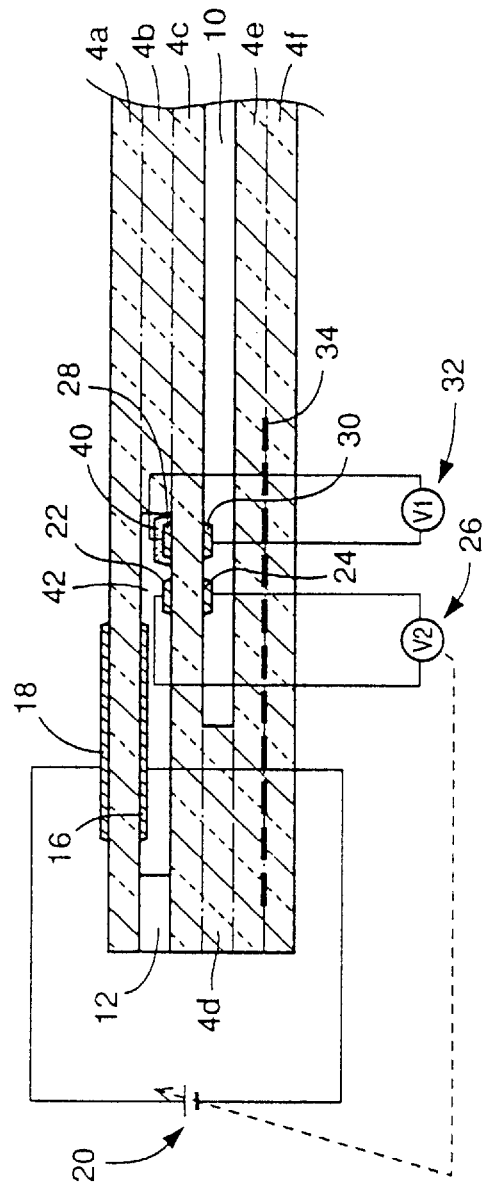
FIG.2(A)
FIG.2(B)

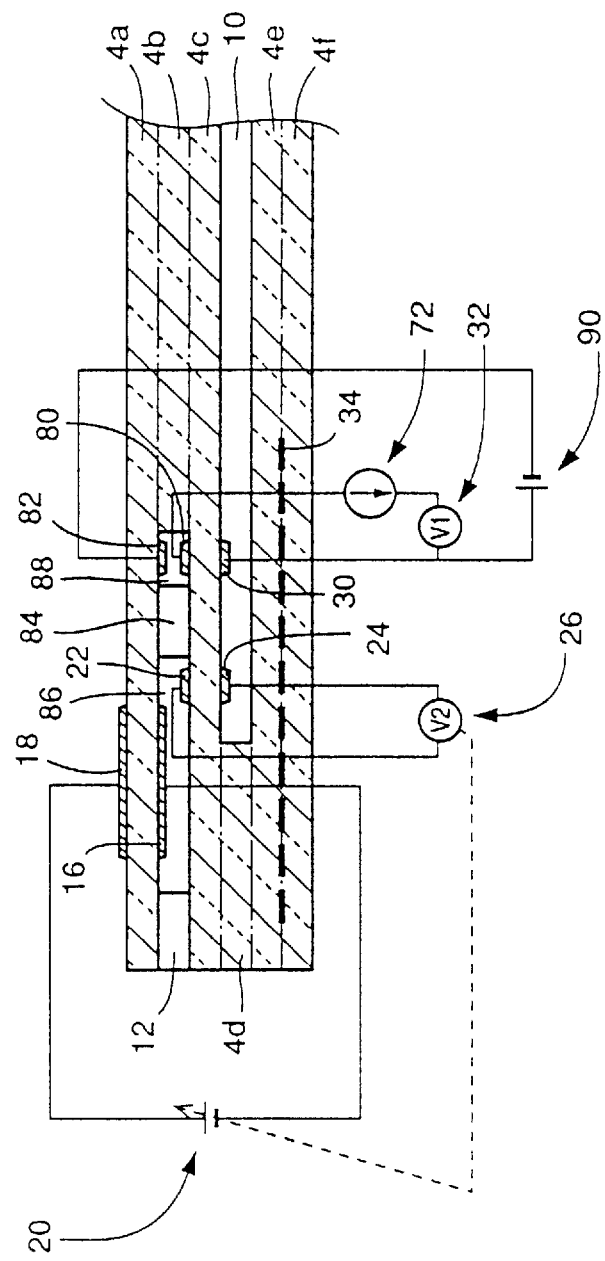

NO$_X$ SENSOR AND METHOD OF MEASURING NO$_X$

This is a Continuation of application Ser. No. 08/732,599 filed Oct. 15, 1996 pending.

BACKGROUND OF THE INVENTION

1. Field of the Invention

The present invention relates to a NOx sensor and a method of measuring NOx. In particular, the present invention relates to improvement in a sensor directed to a combustion gas as a measurement gas, for measuring NOx as a measurement gas component in such a gas, and a method capable of advantageously measuring NOx.

2. Description of the Related Art

Various measuring methods and devices have been proposed for determining the concentration of NOx in a measurement gas. A known method, for example, employs a sensor comprising a Pt electrode and an Rh electrode formed on an oxygen ion-conductive solid electrolyte such as zirconia. This method utilizes the ability of Rh to reduce NOx so that an electromotive force generated between the two electrodes is measured. However, a problem arises in that such a sensor tends to suffer from an influence of noise, since the electromotive force varies to a great extent depending on a change in concentration of oxygen contained in a combustion gas as a measurement gas, while the electromotive force varies to a small extent in response to a change in concentration of NOx. On the other hand, a reducing gas such as CO is indispensable for such a sensor in order to induce the ability to reduce NOx. However, in general, a large amount of NOx is produced under a combustion condition concerning an excessively small amount of fuel, in which an amount of produced CO is less than the amount of produced NOx, resulting in a drawback that measurement cannot be performed for a combustion gas discharged under such a combustion condition.

Another method of measuring NOx is also known, based on a combination of a set of electrochemical pumping cell and sensing cell including Pt electrodes and oxygen-ion conductive solid electrolyte, and another set of electrochemical pumping cell and sensing cell including Rh electrodes and oxygen-ion conductive solid electrolyte, as disclosed in Japanese Laid-open Patent Publication Nos. 63-38154 and 64-39545. In this method, NOx is measured on the basis of a difference between values of pumping currents. Other methods are disclosed, for example, in Japanese Laid-open Patent Publication Nos. 1-277751 and 2-1543. In one method, two pairs, i.e., a first pair and a second pair of electrochemical pumping cell and sensing cell are prepared. A limiting pumping current is measured by using a sensor comprising the first pair of pumping and sensing cells, under a partial pressure of oxygen at which NOx is not reduced, while a limiting pumping current is measured by using a sensor comprising the second pair of pumping and sensing cells, under a partial pressure of oxygen at which NOx is reduced, so that a difference between the measured limiting pumping currents is determined. In another method, a sensor comprising a pair of pumping cell and sensing cell is used, in which a difference in limiting current is measured by switching the partial pressure of oxygen in a measurement gas between a partial pressure of oxygen at which NOx is reduced and a partial pressure of oxygen at which NOx is not reduced.

In the aforementioned methods of measuring NOx, however, an extremely small part of the value of the limiting current is based on the objective NOx, and the most part of the value of the limiting current is occupied by electric power caused by oxygen contained in a large amount in ordinary cases. Therefore, a small current value corresponding to NOx is determined from a difference between two large current values. Accordingly, in the case of the method based on the use of the one set of sensor, problems arise in that the NOx cannot be continuously measured, the operating response is inferior, and the accuracy is inferior. On the other hand, in the case of the method based on the use of the two sets of sensors, an error is likely to occur in a measured value if the oxygen concentration in a measurement gas greatly changes. Therefore, this method cannot be employed in automobile applications, for example, where the oxygen concentration in a measurement gas varies to a large extent. This inconvenience arises from the fact that the dependency of pumping current on oxygen concentration concerning one sensor is different from that concerning the other sensor. In the case of an automobile, for example, the oxygen concentration in exhaust gas is generally several percentages under a running condition of an air/fuel ratio of 20, whereas the NOx concentration is several hundreds of ppm. The concentration of NOx is about $\frac{1}{100}$ of the concentration of oxygen. Therefore, only a slight difference in the dependency of pumping current on oxygen concentration brings about a situation in which a difference in the limiting current value corresponding to a change in oxygen concentration is larger than an amount of change in the limiting current based on NOx to be measured. In addition, if a diffusion rate-determining means formed in the pumping cell is clogged with oil ash in the exhaust gas, the pumping current may be undesirably changed, resulting in reduced accuracy. Further, if the temperature of the exhaust gas greatly varies, a measured value may involve some abnormality. Moreover, a difference in chronological change in any characteristic between the two sensors, if any, may directly lead to measuring errors, resulting in a drawback that the entire system is made undurable for use over a long period of time.

The oxygen present in the measurement gas causes various problems upon measurement of NOx, as described above. Accordingly, it has been strongly desired to solve these problems.

In order to solve the problems described above, the present inventors have revealed a new measuring system in Japanese Patent Application No. 7-48551. In this system, a measurement gas component having bonded oxygen, such as NOx, contained in a measurement gas can be measured continuously and accurately with good response over a long period of time without being affected by the oxygen concentration in the measurement gas or any change thereof, by utilizing first and second electrochemical pumping cells arranged in series.

Namely, in the previously proposed new system, a measurement gas containing a measurement gas component having bonded oxygen to be measured is successively introduced from an external measurement gas-existing space into first and second processing zones under predetermined diffusion resistances respectively. At first, in the first processing zone, the partial pressure of oxygen is controlled to have a low value which does not substantially affect measurement of an amount of the measurement gas component by pumping out oxygen in the atmosphere by using a first electrochemical pumping cell. In the second processing zone, the measurement gas component in the atmosphere introduced from the first processing zone is reduced or decomposed. Oxygen produced by the reduction or decomposition is pumped out by the aid of an oxygen-pumping action effected by a second electrochemical pumping cell. Thus a pumping current flowing through the second electrochemical pumping cell is detected to obtain a detected value from which the amount of the measurement gas component in the measurement gas is determined.

However, as a result of further investigation by the present inventors on such a new measuring system, the sensor concerning the new measuring system described above has been clarified to have the following problem. Namely, measurement of a measurement gas component at a low concentration, for example, measurement of NOx at several ppm gives a pumping current of about several tens of nA detected by the second electrochemical pumping cell, which is small as a detection signal.

SUMMARY OF THE INVENTION

Thus the present invention has been made in order to solve the problems involved in the NOx sensor concerning the previously proposed new system for measuring the NOx concentration in the measurement gas, an object of which is to provide a NOx sensor and a method of measuring NOx, in which a large change in signal can be obtained upon measurement of a concentration of low concentration NOx in a measurement gas, making it possible to perform measurement continuously and accurately with good response over a long period of time.

In order to achieve the object described above, according to a significant aspect of the present invention, there is provided a NOx sensor for measuring an amount of NOx in a measurement gas by measuring an amount of oxygen produced by reducing NOx in the measurement gas with a NOx-reducing catalyst, the NOx sensor comprising (a) a first internal space communicating with an external measurement gas-existing space, (b) a first diffusion rate-determining means for introducing the measurement gas from the measurement gas-existing space into the first internal space under a predetermined diffusion resistance, (c) an electrochemical pumping cell comprising a first oxygen ion-conductive solid electrolyte and a pair of electrodes provided in contact therewith, for pumping out oxygen from the first internal space by applying electric power between the pair of electrodes so that a partial pressure of oxygen in an atmosphere in the first internal space is controlled to have a predetermined low value at which NOx is not substantially reduced, (d) a second internal space communicating with the first internal space and comprising the NOx-reducing catalyst arranged therein, (e) a second diffusion rate-determining means for introducing the controlled atmosphere in the first internal space into the second internal space under a predetermined diffusion resistance, (f) a first electrochemical sensor cell comprising a second oxygen ion-conductive solid electrolyte and a pair of electrodes provided in contact therewith, for reducing NOx existing in an atmosphere in the second internal space with the NOx-reducing catalyst, and outputting an electromotive force corresponding to a partial pressure of oxygen in the atmosphere in the second internal space, defined by oxygen produced by the reduction of NOx, and (g) a voltage-detecting means for detecting the electromotive force outputted from the first electrochemical sensor cell.

Therefore, according to the NOx sensor (first NOx sensor) concerning the present invention as described above, the atmosphere in the first internal space, which has its partial pressure of oxygen controlled to have the predetermined low value by the aide of the electrochemical pumping cell, is introduced into the second internal space communicating with the first internal space through the second diffusion rate-determining means. NOx is reduced or decomposed by the NOx-reducing catalyst in the second internal space. The partial pressure of oxygen in the second internal space is increased by oxygen produced by the reduction of NOx. Thus a pressure gradient of partial pressure of oxygen is brought about between the second internal space and the first internal space. Oxygen pretends to flow in a direction to counteract the pressure gradient, i.e., from the second internal space to the first internal space. However, the pressure resistance is maintained by the predetermined diffusion resistance possessed by the second diffusion rate-determining means. Thus the partial pressure of oxygen in the second internal space is equilibrated at a value which is higher than the partial pressure of oxygen in the first internal space, corresponding to a concentration of oxygen produced by the reduction or decomposition of NOx, in other words, corresponding to a NOx concentration in the measurement gas. The electromotive force, which corresponds to the partial pressure of oxygen in the atmosphere in the second internal space, is detected on the basis of the output from the electrochemical sensor cell. Accordingly, even when the amount of produced oxygen is minute upon measurement of NOx concentration of a low concentration, a large change in electromotive force can be measured.

In a preferred embodiment of the NOx sensor according to the present invention, the NOx-reducing catalyst also serves as the electrode arranged in the second internal spaced, of the pair of electrodes for constituting the electrochemical sensor cell. Accordingly, the NOx sensor can be formed in a compact conformation.

In another preferred embodiment, the NOx sensor according to the present invention comprises a sensor element having an integrated structure including the first and second oxygen ion-conductive solid electrolytes, wherein the sensor element integrally includes the first and second internal spaces, the first and second diffusion rate-determining means, the electrochemical pumping cell, and the electrochemical sensor cell. Accordingly, the NOx sensor according to the present invention can be formed in a more compact conformation. Moreover, the NOx sensor according to the present invention can be advantageously produced from the viewpoint of cost and applicability to mass production.

In still another preferred embodiment, the NOx sensor according to the present invention further comprises a partial oxygen pressure-detecting means for detecting the partial pressure of oxygen in the atmosphere in the first internal space, wherein the partial pressure of oxygen in the atmosphere in the first internal space is controlled by controlling an amount of electric power application between the pair of electrodes of the electrochemical pumping cell on the basis of a value of partial pressure of oxygen detected by the partial oxygen pressure-detecting means. According to this embodiment, the partial pressure of oxygen in the first internal space can be maintained at a predetermined value with a high degree of accuracy.

In still another preferred embodiment of the NOx sensor according to the present invention, a reference gas-existing space is provided in the integrated structure of the sensor element independently from the first and second internal spaces, and the partial oxygen pressure-detecting means is constructed by a second electrochemical sensor cell comprising an oxygen ion-conductive solid electrolyte extending between the reference gas-existing space and the first internal space, a second reference electrode provided in contact with the solid electrolyte located on the reference gas-existing space, and a second measuring electrode provided in contact with the solid electrolyte located on the first internal space. According to such an arrangement, an absolute value of the partial pressure of oxygen in the first internal space is determined easily and accurately by the second electrochemical sensor cell as the partial oxygen pressure-detecting means on the basis of a known partial pressure of oxygen in the reference gas-existing space. Moreover, the NOx sensor according to the present invention can be formed in a more compact conformation.

In still another preferred embodiment of the NOx sensor according to the present invention, the reference gas-existing space is open at an aperture of the sensor element exposed to atmospheric air, and atmospheric air as a reference gas is introduced into the reference gas-existing space through the aperture. Accordingly, it is realized, based on a simple structure, that the absolute value of the partial pressure of oxygen in the first internal space is detected on the basis of a partial pressure of oxygen of atmospheric air by the aid of the second electrochemical sensor cell as the partial oxygen pressure-detecting means.

In still another preferred embodiment of the NOx sensor according to the present invention, the first electrochemical sensor cell uses the oxygen ion-conductive solid electrolyte extending between the second internal space and the reference gas-existing space, as the second oxygen ion-conductive solid electrolyte, and the pair of electrodes of the first electrochemical sensor cell are constructed by a first measuring electrode provided in contact with the solid electrolyte located on the second internal space and a first reference electrode provided in contact with the solid electrolyte located on the reference gas-existing space. According to this embodiment, an absolute value of the partial pressure of oxygen in the second internal space is determined easily and accurately by the first electrochemical sensor cell on the basis of a known partial pressure of oxygen in the reference gas-existing space. Moreover, the NOx sensor according to the present invention can be formed in a more compact conformation.

In still another preferred embodiment of the NOx sensor according to the present invention, a layer of the NOx-reducing catalyst is provided on the first measuring electrode. Accordingly, it is possible to use, for the first measuring electrode, a material which is poor in ability to reduce NOx at a temperature at which the NOx sensor is used, thereby increasing the degree of freedom of material selection for the first measuring electrode.

In still another preferred embodiment of the NOx sensor according to the present invention, the second diffusion rate-determining means and/or the second internal space is composed of a porous material having a predetermined diffusion resistance. When this embodiment is adopted, the sensitivity for detecting the NOx concentration can be improved owing to the diffusion resistance possessed by the porous material. The degree of freedom of design is increased, for example, for the shape and arrangement position of the second diffusion rate-limiting means and/or the second internal space. Thus both of the improvement in performance of the NOx sensor and the applicability to mass production can be achieved.

In still another preferred embodiment of the NOx sensor according to the present invention, the second diffusion rate-determining means and the second internal space are constructed by one porous material having a predetermined diffusion resistance, and arranged in the first internal space, and the first measuring electrode and the second measuring electrode are arranged adjacent to one another with respect to a direction of diffusion of the atmosphere in the first internal space. It is desirable that the first measuring electrode and the second measuring electrode are arranged as close as possible with respect to the diffusing direction.

According to the NOx sensor of the present invention having the arrangement as described above, the second diffusion rate-determining means and the second internal space are constructed by one porous material having the predetermined diffusion resistance, and arranged in the first internal space. Accordingly, the structure is simplified, and the applicability to mass production is further improved. Moreover, the first measuring electrode and the second measuring electrode are arranged adjacent to one another with respect to the direction of diffusion of the atmosphere in the first internal space. Accordingly, it is possible to decrease the change in electromotive force of the first electrochemical sensor cell, i.e., the measuring error for the NOx concentration, caused by the change in distribution of oxygen concentration existing in the gas-diffusing direction depending on the oxygen concentration in the measurement gas.

In still another preferred embodiment of the NOx sensor according to the present invention, the first measuring electrode and the second measuring electrode are arranged in parallel with respect to the direction of diffusion of the atmosphere in the first internal space. Accordingly, it is possible to further increase the effect to decrease the measuring error for the NOx concentration, caused by the change in distribution of oxygen concentration existing in the gas-diffusing direction depending on the oxygen concentration in the measurement gas.

In still another preferred embodiment, the NOx sensor according to the present invention further comprises a third electrochemical sensor cell for detecting, in the second internal space, the partial pressure of oxygen in the atmosphere introduced from the first internal space into the second internal space through the second diffusion rate-determining means, wherein control of the electrochemical pumping cell, which is effected by the second electrochemical sensor cell, is corrected on the basis of a value of partial pressure of oxygen detected by the third electrochemical sensor cell.

According to the NOx sensor of the present invention having the arrangement as described above, the control of the electrochemical pumping cell, which is effected by the second electrochemical sensor cell, is corrected on the basis of the value of partial pressure of oxygen in the atmosphere in the vicinity of the first electrochemical sensor cell in the second internal space. Accordingly, the value of partial pressure of oxygen is stably maintained to be constant. Thus it is possible to decrease the change in electromotive force of the first electrochemical sensor cell, i.e., the measuring error for the NOx concentration, even if the change or the error is extremely large, caused by the change in distribution of oxygen concentration existing in the measurement gas depending on the oxygen concentration in the measurement gas.

In still another preferred embodiment of the NOx sensor according to the present invention, a porous material layer having a predetermined diffusion resistance is provided around the first measuring electrode of the first electrochemical sensor cell arranged in the second internal space. Accordingly, the partial pressure of oxygen in the porous material layer around the first measuring electrode is equilibrated, owing to the diffusion resistance possessed by the porous material layer, at a value which is higher than the partial pressure of oxygen in the second internal space, corresponding to the NOx concentration in the measurement gas. Thus the detecting sensitivity of the NOx sensor is increased.

In still another preferred embodiment, the NOx sensor according to the present invention further comprises a heating means capable of heating the first internal space and the second internal space to a predetermined temperature respectively. Accordingly, it is possible to increase the accuracy in detection of partial pressure of oxygen effected by each of the electrochemical sensor cells. Moreover, an advantage is obtained in that the electrochemical pumping cell can be subjected to the pumping action more effectively even when the temperature of the measurement gas is low, or it changes.

According to another significant aspect of the present invention, there is provided another NOx sensor (second NOx sensor) capable of achieving the object described above, which lies in a NOx sensor, based on the use of a sensor element having an integrated structure comprising oxygen ion-conductive solid electrolytes, for measuring an amount of NOx in a measurement gas by measuring an amount of oxygen produced by reducing NOx in the measurement gas with a NOx-reducing catalyst arranged in an internal space provided in the sensor element, the NOx sensor comprising (h) a first diffusion rate-determining means for introducing the measurement gas from an external measurement gas-existing space into the internal space in the sensor element under a predetermined diffusion resistance, (i) an electrochemical pumping cell comprising an oxygen ion-conductive solid electrolyte of the sensor element and a pair of electrodes provided in contact therewith, for pumping out oxygen from the internal space by applying electric power between the pair of electrodes so that a partial pressure of oxygen in an atmosphere in the internal space is controlled to have a predetermined low value at which NOx is not substantially reduced, (j) a first electrochemical sensor cell comprising an oxygen ion-conductive solid electrolyte of the sensor element, and a first measuring electrode and a first reference electrode provided in contact therewith, the first measuring electrode being located on the internal space and having a porous structure to function as the NOx-reducing catalyst as well, and the first reference electrode being located on a reference gas-existing space provided in the sensor element, wherein NOx existing in an atmosphere in the internal space is reduced in the porous structure of the first measuring electrode, and an electromotive force is outputted corresponding to a partial pressure of oxygen in an atmosphere in the porous structure, defined by oxygen produced by the reduction of NOx, (k) a constant current power source, provided on an electromotive force-outputting circuit including the first measuring electrode and the first reference electrode of the first electrochemical sensor cell, for allowing a constant current to flow so that oxygen is pumped out from the first measuring electrode to the first reference electrode, and allowing the partial pressure of oxygen in the atmosphere in the porous structure of the first measuring electrode to have a predetermined value at which NOx is reduced, and (l) a voltage-detecting means, provided on the electromotive force-outputting circuit of the first electrochemical sensor cell, for detecting the electromotive force outputted from the first electrochemical sensor cell.

According to the second NOx sensor of the present invention as described above, the oxygen exists in the atmosphere in the internal space having the partial pressure of oxygen controlled to have the predetermined low value by the aid of the electrochemical pumping cell. The oxygen is introduced into the inside of the first measuring electrode in an amount always corresponding to a previously set current value of the constant current power source in a state in which the partial pressure of oxygen in the porous structure is lower than that in the internal space by an amount corresponding to pressure loss involved in the diffusion resistance possessed by the first measuring electrode having the porous structure, by the aid of the pumping action effected by the constant current power source. Subsequently, the oxygen is pumped out from the inside of the first measuring electrode to the reference gas-existing space. On the other hand, NOx in the atmosphere diffuses into the first measuring electrode under the predetermined diffusion resistance, which is reduced or decomposed by the first measuring electrode in the vicinity of the surface of the first measuring electrode. The partial pressure of oxygen in the atmosphere in the porous structure of the first measuring electrode is increased by oxygen produced by the reduction or decomposition of NOx. However, the pressure of oxygen in the porous structure is lower than that in the internal space by an amount corresponding to pressure loss when the NOx concentration is zero. In addition, the first measuring electrode has the diffusion resistance. Accordingly, the produced oxygen in the first measuring electrode scarcely diffuses to the internal space. Therefore, any change in NOx concentration in the measurement gas results in a large change in partial pressure of oxygen in the porous structure. Thus the constant current power source greatly changes the voltage applied to the first electrochemical sensor cell in order to continuously allow the current having the previously set value to flow through the electromotive force-outputting circuit, depending on the change in partial pressure of oxygen in the porous structure of the first measuring electrode. The voltage-detecting means detects the change in voltage applied to the first electrochemical sensor cell by the constant current power source, corresponding to the partial pressure of oxygen in the atmosphere in the porous structure, defined by the produced oxygen as described above. Accordingly, even a slight amount of produced oxygen can be measured as a large change in voltage. Thus it is possible to increase the sensitivity for detecting the NOx concentration.

In a preferred embodiment, the second NOx sensor according to the present invention further comprises a partial oxygen pressure-detecting means for detecting the partial pressure of oxygen in the atmosphere in the internal space, wherein the partial pressure of oxygen in the atmosphere in the internal space is controlled by controlling an amount of electric power application between the pair of electrodes of the electrochemical pumping cell on the basis of a value of partial pressure of oxygen detected by the partial oxygen pressure-detecting means. Accordingly, the partial pressure of oxygen in the atmosphere in the internal space can be maintained at a predetermined value with a high degree of accuracy, in the same manner as the first NOx sensor described above.

In another preferred embodiment of the second NOx sensor according to the present invention, the partial oxygen pressure-detecting means is constructed by the oxygen ion-conductive solid electrolyte of the sensor element, a second measuring electrode located on the internal space, provided in contact therewith, and a second reference electrode located on the reference gas-existing space. Accordingly, the NOx sensor according to the present invention can be formed in a more compact conformation in the same manner as the first NOx sensor described above.

In still another preferred embodiment of the second NOx sensor according to the present invention, a porous material layer having a predetermined diffusion resistance is provided around the first measuring electrode of the electrochemical sensor cell. Accordingly, it is possible to more effectively suppress the diffusion of oxygen produced by the reduction or decomposition of NOx, from the first measuring electrode to the internal space. Thus the sensitivity for detecting the NOx concentration is further improved.

In still another preferred embodiment of the second NOx sensor according to the present invention, the first and second measuring electrodes are arranged adjacent to one another with respect to a direction of diffusion of the atmosphere in the internal space. Accordingly, it is possible to obtain the function and effect equivalent to those obtained in the first NOx sensor described above.

In still another preferred embodiment of the second NOx sensor according to the present invention, the first and second measuring electrodes are arranged in parallel with respect to the direction of diffusion of the atmosphere in the internal space. Accordingly, it is possible to further enhance the effect to decrease the measuring error for the NOx concentration, caused by the distribution of oxygen concentration existing in the gas-diffusing direction, in the same manner as the first NOx sensor described above.

In still another preferred embodiment of the second NOx sensor according to the present invention, the internal space is divided into a first internal space communicating with the external measurement gas-existing space through the first diffusion rate-determining means, and a second internal space into which an atmosphere in the first internal space is introduced through a second diffusion rate-determining means under a predetermined diffusion resistance, the electrochemical pumping cell is located on the first internal space, the first electrochemical sensor cell is located on the second internal space, and the NOx sensor further comprises a subsidiary oxygen-pumping means for lowering a partial pressure of oxygen in the atmosphere introduced from the first internal space into the second internal space, to a degree sufficient to reduce NOx in the porous structure of the first measuring electrode of the first electrochemical sensor cell. Advantageously, the subsidiary oxygen-pumping means is constructed by the oxygen ion-conductive solid electrolytes of the sensor element and a pair of electrodes provided in contact therewith.

According to the second NOx sensor of the present invention as described above, NOx is successively introduced into the first internal space and the second internal space. In the respective internal spaces, the oxygen-pumping action is effected by the electrochemical pumping cell and the subsidiary oxygen-pumping means to pump out oxygen. Accordingly, in the first internal space, nothing is required other than the oxygen concentration is lowered to the degree sufficient to control the partial pressure of oxygen by the aid of the subsidiary oxygen-pumping means in the subsequent second internal space. In the second internal space, the value of partial pressure of oxygen, which has been lowered in the first internal space, is further lowered so that the partial pressure of oxygen may be accurately controlled to have the value of partial pressure of oxygen which does not substantially affect measurement of the amount of the measurement gas component. Therefore, even when the oxygen concentration of the measurement gas is high, and hence the change in electromotive force of the first electrochemical sensor cell, caused by the change in distribution of oxygen concentration in the measurement gas depending on the oxygen concentration in the measurement gas, i.e., the measuring error for measurement of NOx concentration is extremely large, the change in electromotive force generated in the first electrochemical sensor cell is not affected by any influence thereof. Thus an obtained value accurately corresponds to the amount of the measurement gas component existing in the measurement gas, making it possible to perform accurate measurement. In addition, the NOx concentration in the measurement gas can be accurately measured in a state in which the partial pressure of oxygen in the first internal space is previously set to be a predetermined value which is sufficiently higher than the partial pressure of oxygen in the second internal space. Accordingly, even when inflammable gases such as CO, HC, and $H_2$ are present in the measurement gas in a mixed manner, the inflammable gases can be removed by oxidation in the first internal space. Thus it is possible to decrease the measuring error for the NOx concentration, due to interference by the inflammable gases in the second internal space, as small as possible.

In still another preferred embodiment, the second NOx sensor according to the present invention further comprises a heating means capable of heating the internal space to a predetermined temperature. Accordingly, it is possible to obtain the same function and effect as those obtained in the first NOx sensor described above.

According to other significant aspects of the present invention, the following methods of measuring a NOx component in a measurement gas are also provided, wherein the measuring methods may be advantageously carried out by using the foregoing NOx sensors.

One of the methods of measuring NOx components in measurement gases according to the present invention is carried out concerning the foregoing first NOx sensor, which lies in a method of measuring NOx, comprising the steps of introducing a measurement gas from an external measurement gas-existing space into a first internal space under a predetermined diffusion resistance, controlling a partial pressure of oxygen in an atmosphere in the first internal space to have a predetermined low value at which NOx is not substantially reduced, by the aid of an oxygen-pumping action effected on the first internal space by an electrochemical pumping cell, introducing the controlled atmosphere in the first internal space into a second internal space under a predetermined diffusion resistance, reducing, in the second internal space, NOx existing in an atmosphere with a NOx-reducing catalyst, and outputting, with the use of an electrochemical sensor cell, an electromotive force corresponding to a partial pressure of oxygen in the atmosphere in the second internal space, defined by oxygen produced by the reducing step to obtain a detected output value from which an amount of NOx in the measurement gas is determined.

Preferably, in the measuring method according to the present invention, the partial pressure of oxygen in the atmosphere in the first internal space is controlled to have the constant value by detecting the partial pressure of oxygen in the atmosphere in the first internal space to obtain a detected value on the basis of which a power source voltage is changed so that the oxygen-pumping action effected by the electrochemical pumping cell is controlled.

According to the present invention, there is provided another measuring method concerning the foregoing second NOx sensor, which lies in a method of measuring NOx, comprising the steps of introducing a measurement gas from an external measurement gas-existing space into an internal space under a predetermined diffusion resistance, controlling a partial pressure of oxygen in an atmosphere in the internal space to have a predetermined low value at which NOx is not substantially reduced, by the aid of an oxygen-pumping action effected on the internal space by an electrochemical pumping cell, reducing NOx in a porous structure by allowing a constant current to flow through an electrochemical sensor cell comprising a measuring electrode having the porous structure located on the internal space so that a partial pressure of oxygen in an atmosphere in the porous structure has a predetermined value at which NOx is reduced, and outputting, with the use of the electrochemical sensor cell, an electromotive force corresponding to a partial pressure of oxygen defined by oxygen produced by the reducing step to obtain a detected output value from which an amount of NOx in the measurement gas is determined.

Preferably, in the second measuring method according to the present invention, the partial pressure of oxygen in the atmosphere in the internal space is controlled to have the constant value by detecting the partial pressure of oxygen in the atmosphere in the internal space to obtain a detected value on the basis of which a power source voltage is changed so that the oxygen-pumping action effected by the electrochemical pumping cell is controlled.

The above and other objects, features and advantages of the present invention will become more apparent from the following description when taken in conjunction with the accompanying drawings in which a preferred embodiment of the present invention is shown by way of illustrative example.

DESCRIPTION OF THE DRAWINGS

FIG. 2(A) explanatorily shows a plan view corresponding to FIG. 1(A) of a modified embodiment of the NOx sensor according to the present invention, and FIG. 2 (B) explanatorily shows a cross-sectional view corresponding to FIG. 1(B).

FIG. 6 explanatorily shows a modified embodiment of the second embodiment of the NOx sensor according to the present invention, explanatorily illustrating a cross-sectional view corresponding to FIG. 1(B).

DESCRIPTION OF THE PREFERRED EMBODIMENTS

Figure 1A:
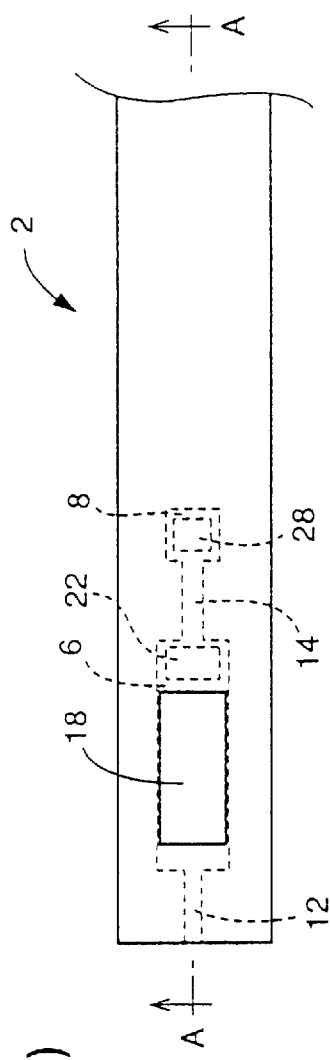
FIG. 1(A) explanatorily shows a plan view of a first embodiment of the NOx sensor according to the present invention, and FIG. 1(B) explanatorily shows an enlarged view of principal components, taken along a cross section of I—I shown in FIG. 1(A).

In order to clarify the present invention more specifically, the system of the present invention will be explained in detail below with reference to embodiments illustrated in the drawings.

Figure 1B:
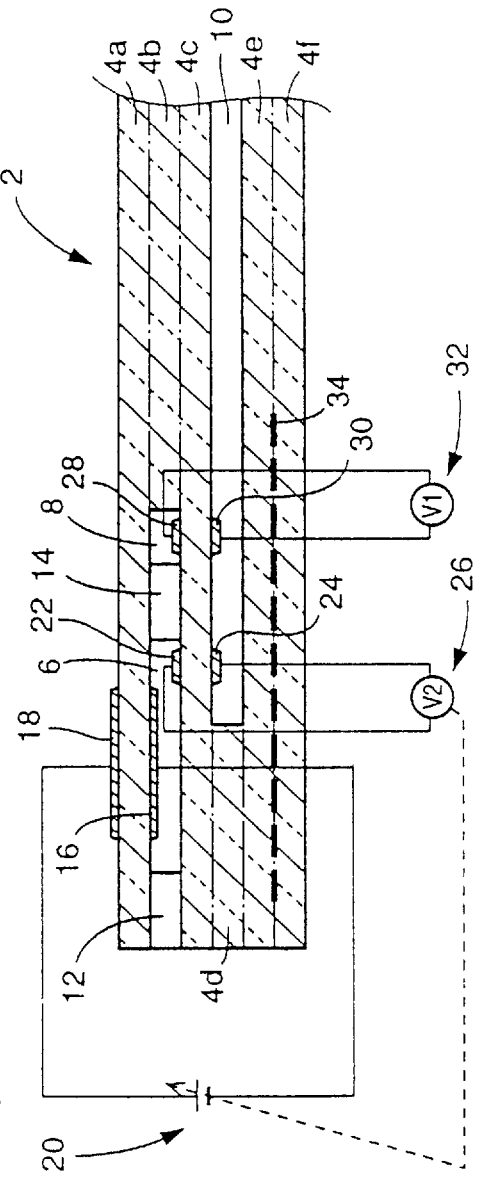

At first, FIG. 1(A) and FIG. 1(B) illustrate a representative example of a NOx sensor (first NOx sensor) as a first embodiment according to the present invention. FIG. 1(A) shows a plan view of the sensor, and FIG. 1(B) explanatorily shows an enlarged view of principal components, taken along a cross section of I—I shown in FIG. 1(A).

With reference to FIG. 1(A) and FIG. 1(B), reference numeral 2 indicates a sensor element having a slender and lengthy plate-shaped configuration. As shown in FIG. 1(B), the sensor element 2 is a plate-shaped object having an integrated structure comprising a plurality of dense and airtight oxygen ion-conductive solid electrolyte layers $4a$, $4b$, $4c$, $4d$, $4e$, $4f$ stacked up with each other. Each of the solid electrolyte layers $4a$ to $4f$ is formed of a known oxygen ion-conductive solid electrolyte material such as zirconia ceramics. The sensor element 2 having the integrated structure is produced by firing stacked unfired solid electrolyte layers into the integrated structure in the same manner as those hitherto performed.

The sensor element 2 having the integrated structure described above includes a first internal space 6 and a second internal space 8 each having a rectangular and plane configuration and individually constructed such that the first internal space 6 is located on a distal side of the element. A reference air-introducing passage 10, which serves as a reference gas-existing space, extends in a longitudinal direction of the sensor element 2. The reference air-introducing passage 10 is provided independently from the first and second internal spaces 6, 8, while overlapping vertically with the first and second internal spaces 6, 8. The reference air-introducing passage 10 is open at the proximal end of the sensor element 2 to make communication with atmospheric air. In this embodiment, the first and second internal spaces 6, 8 are formed such that spaces corresponding thereto formed through the solid electrolyte layer $4b$ are closed by the upper and lower solid electrolyte layers $4a$, $4c$. Accordingly, the first and second internal spaces 6, 8 are substantially located on an identical plane. The reference air-introducing passage 10 is formed such that a space corresponding thereto formed through the solid electrolyte layer $4d$ is closed by the upper and lower solid electrolyte layers $4c$, $4e$.

A first diffusion rate-determining passage 12, which serves as a first diffusion rate-determining means for allowing the first internal space 6 to communicate with an external measurement gas-existing space, is formed by cutting out the solid electrolyte layer $4b$ so that the first diffusion rate-determining passage 12 is open at the distal end of the sensor element 2. A measurement gas containing NOx is introduced into the first internal space 6 under a predetermined diffusion resistance through the first diffusion rate-determining passage 12. A second diffusion rate-determining passage 14, which serves as a second diffusion rate-determining means for making communication between the two internal spaces 6,8, is formed through the solid electrolyte layer $4b$ located between the first and second internal spaces 6, 8. An atmosphere in the first internal space 6 is introduced into the second internal space 8 under a predetermined diffusion resistance through the second diffusion rate-determining passage 14.

An inner pumping electrode 16, which is composed of a rectangular porous cermet electrode, is provided on a portion of the solid electrolyte layer 4a exposed to the first internal space 6, in contact therewith. An outer pumping electrode 18, which is also composed of a rectangular porous cermet electrode, is provided on an outer surface portion of the solid electrolyte layer 4a corresponding to the inner pumping electrode 16, in contact therewith. An electrochemical pumping cell is constructed by the electrodes 16, 18 and the solid electrolyte layer 4a. A desired voltage is applied between the two electrodes 16, 18 of the electrochemical pumping cell by using an external variable power source 20, and a current is allowed to flow in a direction from the outer pumping electrode 18 to the inner pumping electrode 16. Thus oxygen in the atmosphere in the first internal space 6 can be pumped out to the external measurement gas-existing space. The porous cermet electrode comprises a metal such as Pt and a ceramic such as $ZrO_2$. However, the inner pumping electrode 16 is arranged in the first internal space 6, which contacts with the measurement gas. Therefore, it is necessary for the inner pumping electrode 16 to use a metal having a weak ability or no ability to reduce the NOx component in the measurement gas. Desirably, the inner pumping electrode 16 comprises, for example, a cermet of $ZrO_2$ and a Pt—Au alloy. As described above, the pumping electrodes 16, 18 generally have a porous structure.

A second measuring electrode 22, which is composed of a porous cermet electrode similarly to the inner pumping electrode 16, is provided on a portion of the solid electrolyte layer 4c exposed to the first internal space 6, in contact therewith. A second reference electrode 24, which is composed of a porous cermet electrode similarly to the outer pumping electrode 18, is provided on a portion of the solid electrolyte layer 4c exposed to the reference air-introducing passage 10, in contact therewith. An electrochemical cell, which serves as a partial oxygen pressure-detecting means, i.e., a second electrochemical sensor cell, is constructed by the second measuring electrode 22, the second reference electrode 24, and the solid electrolyte layer 4c. The partial pressure of oxygen in the atmosphere in the first internal space 6 is detected by measuring an electromotive force generated between the second measuring electrode 22 and the second reference electrode 24, by using a second potentiometer 26, on the basis of a difference in oxygen concentration between the atmosphere in the first internal space 6 and the reference air (atmospheric air) in the reference air-introducing passage 10, as well known in the art. The voltage of the variable power source 20 is controlled on the basis of a value of partial pressure of oxygen in the atmosphere in the first internal space 6, detected by the second potentiometer 26. Thus the pumping action of the electrochemical pumping cell is controlled so that the partial pressure of oxygen in the atmosphere in the first internal space 6 comes to a predetermined low value at which NOx is not substantially reduced in the presence of the inner pumping electrode 16 and the second measuring electrode 22 of the second electrochemical sensor cell.

A rectangular first measuring electrode 28 is provided in the second internal space 8, on a portion of the solid electrolyte layer 4c exposed to the second internal space 8, in contact therewith. The first measuring electrode 28 is composed of a porous cermet comprising zirconia as a ceramic and Rh which is a metal capable of reducing NOx. Thus the first measuring electrode 28 functions as a NOx-reducing catalyst capable of reducing NOx existing in an atmosphere in the second internal space 8. On the other hand, a first reference electrode 30 is provided on the solid electrolyte layer 4c, corresponding to the first measuring electrode 28, so that the first reference electrode 30 is exposed to the inside of the reference air-introducing passage 10. A first electrochemical sensor cell is constructed by the first measuring electrode 28, the first reference electrode 30, and the solid electrolyte layer 4c. As well known, an electromotive force, which is generated between the first measuring electrode 28 and the first reference electrode 30, is outputted on the basis of a difference in oxygen concentration between an atmosphere around the first measuring electrode 28 and an atmosphere around the first reference electrode 30. The electromotive force is measured by a first potentiometer 32. Thus it is possible to detect the partial pressure of oxygen in the atmosphere around the first measuring electrode 28, in other words, the partial pressure of oxygen defined by oxygen produced by reducing or decomposing the measurement gas component (NOx).

A heater 34, which is heated by external power supply, is embedded in the sensor element 2 such that the heater 34 is vertically interposed between the solid electrolyte layers 4e, 4f. Upper and lower surface of the heater 34 are covered with thin layers of ceramic such as alumina, although not shown, in order to obtain electric insulation from the solid electrolyte layers 4e, 4f. In this embodiment, as shown in FIG. 1(B), the heater 34 is arranged over the entire length ranging from the first internal space 6 to the second internal space 8. Thus the internal spaces 6, 8 are heated to a predetermined temperature respectively. Consequently, the electrochemical pumping cell, as a matter of course, as well as the first and second electrochemical sensor cells is heated to and maintained at the predetermined temperature respectively.

In conformity with the arrangement of the sensor element 2 as described above, its distal end is arranged in the measurement gas-existing space. Accordingly, the measurement gas is introduced into the first internal space 6 under the predetermined diffusion resistance through the first diffusion rate-determining passage 12 provided in the sensor element 2. The measurement gas introduced into the first internal space 6 undergoes the oxygen-pumping action evoked by applying a predetermined voltage between the two pumping electrodes 16, 18 which constitute the electrochemical pumping cell so that the partial pressure of oxygen is controlled to have a predetermined value, for example, $10^{-10}$ atm.

In order to control the partial pressure of oxygen in the atmosphere in the first internal space 6 to have the predetermined value, a technique is adopted on the basis of the well known Nernst equation. Namely, the electromotive force between the second measuring electrode 22 and the second reference electrode 24 of the electrochemical sensor cell is measured by using the second potentiometer 26. The voltage (variable power source 20) applied between the two electrodes 16, 18 of the electrochemical pumping cell is controlled so that the electromotive force is, for example, 430 mV (700° C.). Thus the partial pressure of oxygen is controlled to have the objective value of $10^{-10}$ atm. Namely, the voltage of the first electrochemical pumping cell is controlled so that the electromotive force corresponds to a difference between a desired oxygen concentration in the first internal space 6 and an oxygen concentration in the reference air. The first diffusion rate-determining passage 12 serves to reduce the amount of oxygen in the measurement gas diffusing and flowing into the measuring space (first internal space 6) when the voltage is applied to the first electrochemical pumping cell so that the current flowing through the electrochemical pumping cell is suppressed.

A state of partial pressure of oxygen, in which NOx in the atmosphere is not reduced by the inner pumping electrode 16 and the second measuring electrode 22, for example, a state of partial pressure of oxygen, in which the reaction: $NO \rightarrow 1/2N_2 + 1/2O_2$ does not take place, is established in the first internal space 6 even under a heated condition caused by heating by the external measurement gas and the heater 34. If NOx in the measurement gas (or in the atmosphere) is reduced in the first internal space 6, it is impossible to accurately measure NOx in the second internal space 8. In this context, it is necessary to establish the state in the first internal space 6 in which NOx is not reduced by any component (any metal component of the inner pumping electrode 16 and the second measuring electrode 22 in this embodiment) which may concern reduction of NOx.

The measurement gas, which has its partial pressure of oxygen controlled in the first internal space 6 as described above, is introduced into the second internal space 8 through the second diffusion rate-determining passage 14 under the predetermined diffusion resistance. NOx in the measurement gas introduced into the second internal space 8 is reduced or decomposed in accordance with, for example, the reaction: $NO \rightarrow 1/2N_2 + 1/2O_2$ around the first measuring electrode 28 which also functions as a catalyst for reducing NOx, under the heated condition and under the partial pressure of oxygen. The first potentiometer 32 measures an electromotive force generated between the first measuring electrode 28 and the first reference electrode 30 on the basis of a difference between the partial pressure of oxygen in the atmosphere around the first reference electrode 30 and a partial pressure of oxygen in the atmosphere around the first measuring electrode 28, i.e., in the atmosphere in the second internal space 8, defined by oxygen produced by the reduction or decomposition. Accordingly, it is possible to detect the partial pressure of oxygen in the atmosphere in the second internal space 8, in other words, the raised partial pressure of oxygen, defined by oxygen produced by the reduction or decomposition of NOx. Thus the NOx concentration in the measurement gas can be measured. In order to increase the ratio of change in partial pressure of oxygen in the atmosphere in the second internal space 8 based on oxygen produced as described above, it is desirable that the partial pressure of oxygen in the atmosphere in the first internal space 6, and consequently the partial pressure of oxygen in the atmosphere in the second internal space 8 in the absence of NOx is maintained at a sufficiently low value which is, for example, $10^{-10}$ atm.

The partial pressure of oxygen in the atmosphere in the second internal space 8, which is defined and raised by oxygen produced by reducing or decomposing NOx in the measurement gas, tends to decrease on account of diffusion of oxygen in a direction to counteract the pressure gradient of partial pressure of oxygen between the second internal space 8 and the first internal space 6, i.e., from the second internal space 8 to the first internal space 6. However, in the NOx sensor of this first embodiment, the pressure gradient is not completely counteracted because of the predetermined diffusion resistance possessed by the second diffusion rate-determining passage 14. The partial pressure of oxygen in the atmosphere in the second internal space 8 is equilibrated at a value which is higher than the partial pressure of oxygen in the first internal space 6, substantially corresponding to the increased partial pressure of oxygen brought about by oxygen produced by reducing or decomposing NOx in the atmosphere in the second internal space 8, i.e., substantially corresponding to the NOx concentration in the measurement gas. Thus the electromotive force, which corresponds to the partial pressure of oxygen in the atmosphere in the second internal space 8, is detected from the output from the electrochemical sensor cell. Accordingly, even when the amount of produced oxygen is minute upon measurement of the NOx concentration at a low concentration, the NOx concentration can be measured as a large change in electromotive force.

The sensitivity for detecting the NOx concentration can be regulated by changing the cross-sectional area, the cross-sectional shape, and the length of the second diffusion rate-determining passage 14.

The sensitivity for detecting the NOx concentration can be further increased by packing a porous material having a predetermined diffusion resistance into the second diffusion rate-determining passage 14 and/or the second internal passage 8, because of the reason as described above.

In the foregoing embodiment, any one of the inner pumping electrode 16 and the second measuring electrode 22, arranged in the first internal space 6, is required not to reduce or decompose NOx in the atmosphere respectively at the ambient temperature and the controlled partial pressure of oxygen in the internal space respectively. Accordingly, those usable include electrode metals such as Au and Ni having no ability or a weak ability to reduce or decompose NOx. Those advantageously usable include, for example, cermet electrodes comprising the metal described above, and cermet electrodes obtained by using an alloy prepared by adding a metal having no catalytic ability such as Au and Ni described above to a noble metal such as Pt, Pd, and Rh. Desirably, the first measuring electrode 28 arranged in the second internal space 8 is a cermet electrode composed of, for example, Rh capable of reducing or decomposing NOx in the atmosphere at the environmental temperature and the partial pressure of oxygen in the second internal space 8. It is of course possible to use, as the first measuring electrode 28, those obtained by arranging and stacking, on an ordinary electrode, an Rh or Pt electrode, or a catalyst material comprising a NOx-reducing metal carried on a ceramic porous material such as alumina, and those obtained by arranging an Rh catalyst electrode on a Pt electrode.

In any case, the respective electrodes provided for the NOx sensor described above, especially the inner pumping electrode 16 and the measuring electrodes 22, 28 arranged in the respective internal spaces are desirably cermet electrodes composed of an electrode metal and an appropriate ceramic. In particular, as exemplified above, in the case of the use of the first measuring electrode 28 which also functions as a NOx-reducing catalyst, it is desirable to use a porous cermet electrode comprising a ceramic and a known metal capable of reducing NOx such as Rh and Pt. The NOx-reducing catalyst may be provided in the close vicinity of the first measuring electrode 28 of the first electrochemical pumping cell for detecting the partial pressure of oxygen in the second internal space 8. Alternatively, a porous alumina, on which a NOx-reducing catalyst comprising, for example, Rh is carried, may be stacked on the first measuring electrode 28 by means of printing or the like to form a NOx-reducing catalyst layer on the electrode.

It is needless to say that the NOx sensor according to the present invention should not be interpreted such that the NOx sensor is limited to only the structure of the foregoing embodiment. One modified embodiment of the NOx sensor is shown in FIG. 2(A), (B).

The first modified embodiment shown in FIG. 2(A), (B) is different from the foregoing first embodiment, which is specifically characterized in that the second internal space and the second diffusion rate-determining passage as the second diffusion rate-determining means are constructed by one porous material layer 40 having a predetermined diffusion resistance, arranged to cover a first measuring electrode 28, and the first measuring electrode 28 and a second measuring electrode 22 are arranged in series adjacent to one another with respect to a direction of diffusion of an atmosphere in an internal space 42. Namely, the porous material layer 40 is constructed to serve as both of the second diffusion rate-determining passage and the second internal space. The measurement gas, which has its partial pressure of oxygen controlled in the internal space 42, diffuses through the porous material layer 40 under a predetermined diffusion resistance, and arrives at the first measuring electrode 28 arranged at a section under the porous material layer 40. Thus NOx in the measurement gas is reduced by the first measuring electrode 28. An electromotive force, which is defined by oxygen produced by the reduction of NOx, corresponding to a raised partial pressure of oxygen, is generated between the first measuring electrode 28 and the first reference electrode 30. The electromotive force is measured by a first potentiometer 32. Accordingly, the structure of the NOx sensor is simplified. Such a NOx sensor is advantageous from the viewpoint of cost and applicability to mass production.

It is desirable that the first measuring electrode 28 and the second measuring electrode 22 are arranged as nearly as possible in the diffusing direction. Accordingly, it is possible to decrease the change in electromotive force of the first electrochemical sensor cell, i.e., the measuring error for the NOx concentration, caused by the change in distribution of oxygen concentration existing in the gas-diffusing direction depending on the oxygen concentration in the measurement gas.

For example, porous $Al_2O_3$ and $ZrO_2$ are used for the porous material layer 40 having the predetermined diffusion resistance, arranged to cover the first measuring electrode 28.

Figure 3A:
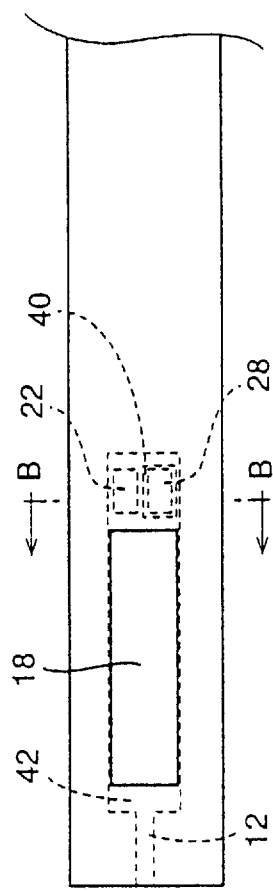
FIG. 3(A) explanatorily shows a plan view corresponding to FIG. 1(A) of another modified embodiment of the NOx sensor according to the present invention, and FIG. 3(B) explanatorily shows an enlarged view of principal components, taken along a cross section of II—II shown in FIG. 3(A).
Figure 3B:
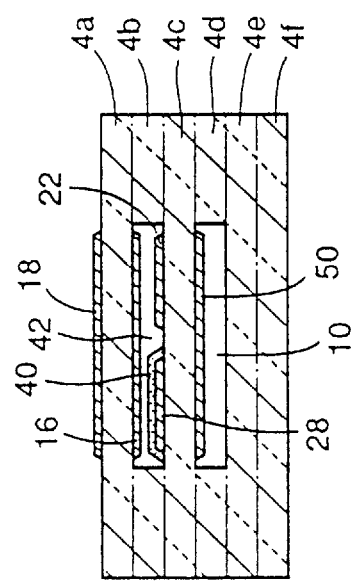

A second modified embodiment shown in FIG. 3(A), (B) is different from the first modified embodiment shown in FIG. 2(A) and FIG. 2(B), which is specifically characterized in that a first measuring electrode 28 is covered with one porous material layer 40 having a predetermined diffusion resistance for constructing the second diffusion rate-determining means and the second internal space, the first measuring electrode 28 and a second measuring electrode 22 are arranged in parallel with respect to an atmosphere-diffusing direction in an internal space 42, and the first and second reference electrodes are provided as one common reference electrode 50. Owing to the arrangement of the first measuring electrode 28 and the second measuring electrode 22, it is possible to further decrease the change in electromotive force of the first electrochemical sensor cell, i.e., the measuring error for the NOx concentration, caused by the change in distribution of oxygen concentration existing in the gas-diffusing direction depending on the oxygen concentration in the measurement gas. In the second modified embodiment, the first measuring electrode 28 and the second measuring electrode 22 may be provided on the solid electrolyte layers 4a, 4c respectively to oppose to one another with the internal space 42 interposed therebetween, while they are arranged in parallel with respect to the atmosphere-diffusing direction in the internal space 42.

Figure 4:
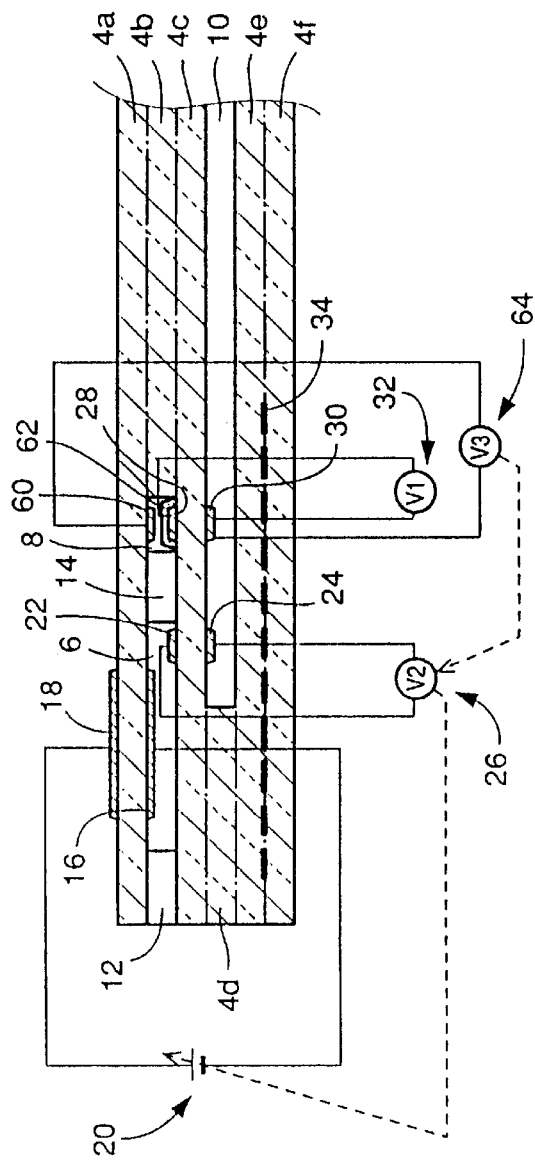
FIG. 4(A) explanatorily shows a cross-sectional view corresponding to FIG. 1(B) of still another modified embodiment of the NOx sensor according to the present invention.
FIG. 4(B) shows a block diagram illustrating a system of pumping voltage control effected in the NOx sensor shown in FIG. 4(A).
Figure 4:
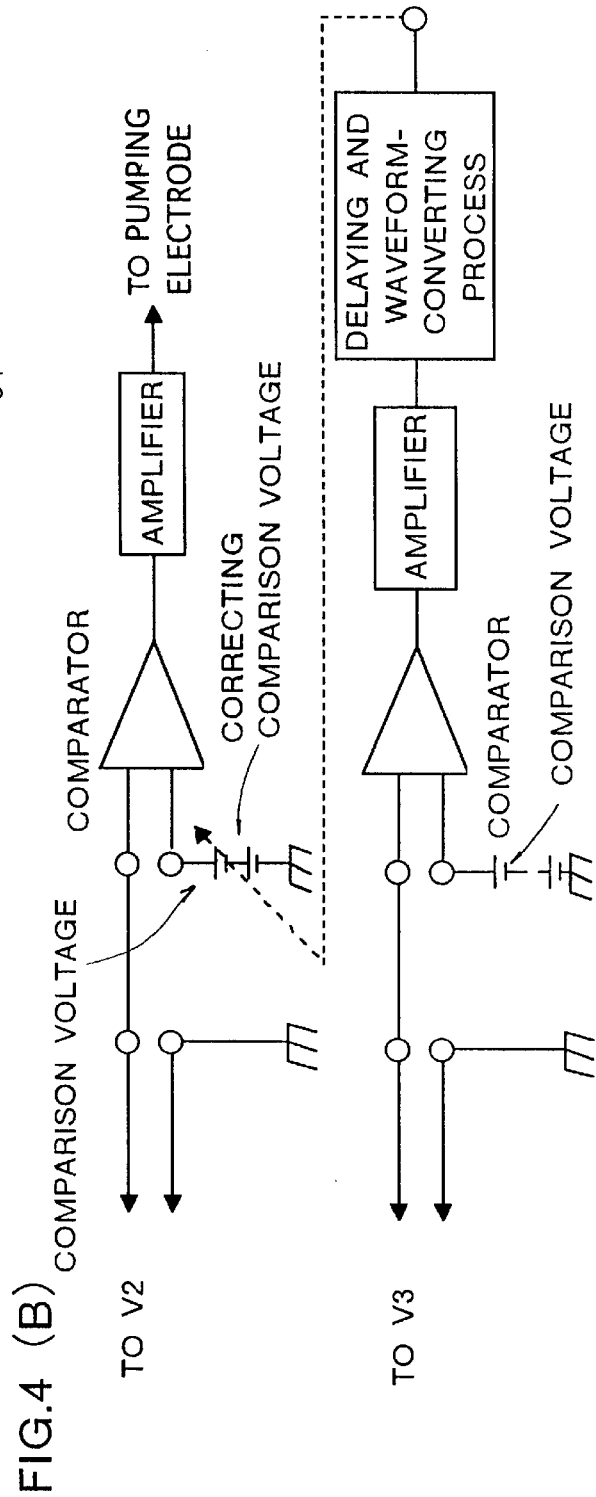

A third modified embodiment shown in FIG. 4(A) is specifically characterized as follows, in addition to the feature of the first embodiment shown in FIG. 1(A), (B). Namely, a porous material layer 62 having a predetermined diffusion resistance is provided around the first measuring electrode 28 of the first electrochemical sensor cell, arranged in the second internal space 8. A third measuring electrode 60 is provided in contact with the solid electrolyte layer 4a located on the second internal space 8 so that the third measuring electrode 60 is opposed to the first measuring electrode 28 with the second internal space 8 interposed therebetween. The third measuring electrode 60, the solid electrolyte layers 4a, 4b, 4c, and the first reference electrode 30 constitute a third electrochemical sensor cell for detecting, in the second internal space 8, the partial pressure of oxygen in the atmosphere introduced from the first internal space 6 into the second internal space 8 through the second diffusion rate-determining passage 14. An electromotive force outputted from the third electrochemical sensor cell is detected by a third potentiometer 64 to obtain a detected value on the basis of which correction is performed for control of the electrochemical pumping cell effected by the second electrochemical sensor cell.

Namely, the partial pressure of oxygen in the measurement gas, which is introduced from the first internal space 6 into the second internal space 8 through the second diffusion rate-determining passage 14, is detected by the third potentiometer 64 on the basis of the electromotive force of the third electrochemical sensor cell constructed by the third measuring electrode 60 arranged in the second internal space 8, the first reference electrode 30, and the solid electrolyte layers 4a, 4b, 4c. The control of partial pressure of oxygen in the first internal space 6, which is performed by the electrochemical pumping cell controlled by the second electrochemical sensor cell, is corrected on the basis of a detected value of partial pressure of oxygen. The measurement gas introduced into the second internal space 8 diffuses under the predetermined diffusion resistance of the porous material layer 62 arranged in the second internal space 8, and arrives at the first measuring electrode 28 arranged at the inner section of the porous material layer 62. Thus NOx is reduced by the first measuring electrode 28. The electromotive force, which is generated between the first measuring electrode 28 and the first reference electrode 30, is measured by the first potentiometer 32.

The control of the electrochemical pumping cell is corrected by regulating a target value of partial pressure of oxygen in the atmosphere in the first internal space 6 concerning the second electrochemical sensor cell which controls the electrochemical pumping cell so that the electromotive force of the third electrochemical sensor cell is maintained to be a constant value. For example, when the partial pressure of oxygen in the atmosphere in the second internal space 8 is raised, namely when the electromotive force of the third electrochemical sensor cell is lowered, the target value of partial pressure of oxygen is lowered. Thus the electrochemical pumping cell is operated so that the partial pressure of oxygen in the atmosphere in the first internal space 6 is lowered. Accordingly, the partial pressure of oxygen in the atmosphere in the first internal space 6, and consequently the partial pressure of oxygen in the atmosphere in the second internal space 8 are lowered.

More specifically, a system as shown in FIG. 4(B) is employed. At first, a voltage value of the third potentiometer 64 is compared with a comparison voltage corresponding to a target value of partial pressure of oxygen in the atmosphere in the second internal space 8, by using a comparator. A difference therebetween is amplified into a predetermined magnitude by using an amplifier, followed by being subjected to a delaying and waveform-converting process to avoid oscillation upon feedback control so that a correcting comparison voltage is obtained. The correcting comparison voltage is applied in series to a comparison voltage for the second potentiometer 26 which corresponds to a target value of partial pressure of oxygen in the atmosphere in the first internal space 6. Thus the comparison voltage for the second potentiometer 26 is corrected. After that, a voltage value of the second potentiometer 26 is compared with the corrected comparison voltage for the second potentiometer 26 by using a comparator. A difference therebetween is amplified by an amplifier into a predetermined magnitude to obtain a voltage which is applied to the electrochemical pumping cell so that the electrochemical pumping cell is operated.

According to the NOx sensor as described above, even when the oxygen concentration in the measurement gas is high, and hence the change in electromotive force of the first electrochemical sensor cell, i.e., the measuring error for the NOx concentration, which is caused by the change in distribution of oxygen concentration in the measurement gas depending on the oxygen concentration in the measurement gas, is extremely large, the electrochemical pumping cell is controlled by the second electrochemical sensor cell on the basis of the value of partial pressure of oxygen in the atmosphere in the vicinity of the first electrochemical sensor cell. Accordingly, the value of partial pressure of oxygen is stably maintained to be constant. Therefore, it is possible to further decrease the measuring error for the NOx concentration resulting from the distribution of oxygen concentration in the measurement gas. Moreover, the porous material layer 62 having the predetermined diffusion resistance is provided around the first measuring electrode 28 of the first electrochemical sensor cell. Accordingly, the sensitivity for detecting the NOx concentration is also improved.

In the foregoing first embodiment, the concentration of NOx is determined by detecting the change in partial pressure of oxygen in the second internal space caused by oxygen produced by reducing or decomposing NOx in the second internal space, as the change in value of the electromotive force outputted by the first electrochemical sensor cell. However, in the present invention, a NOx sensor and a method of measuring NOx as described below are also advantageously adopted in order to measure the NOx concentration in the measurement gas.

Namely, an electrochemical sensor cell is formed, which includes a first measuring electrode arranged in a predetermined internal space, having a porous structure and functioning as a NOx-reducing catalyst as well. A constant current is allowed to flow so that oxygen is pumped out from the first measuring electrode to a first reference electrode, by using a constant current power source provided on an electromotive force-outputting circuit comprising the first measuring electrode and the first reference electrode of the electrochemical sensor cell. Under this condition, NOx existing in an atmosphere in the internal space is reduced or decomposed in a porous structure of the first measuring electrode. An electromotive force, which corresponds to a partial pressure of oxygen in an atmosphere in the porous structure, defined by oxygen produced by the reduction or decomposition of NOx, is detected from an output from the electrochemical sensor cell to obtain a detected value from which a NOx concentration in a measurement gas is determined. An example is shown in FIG. 5(A), (B).

Figure 5A:
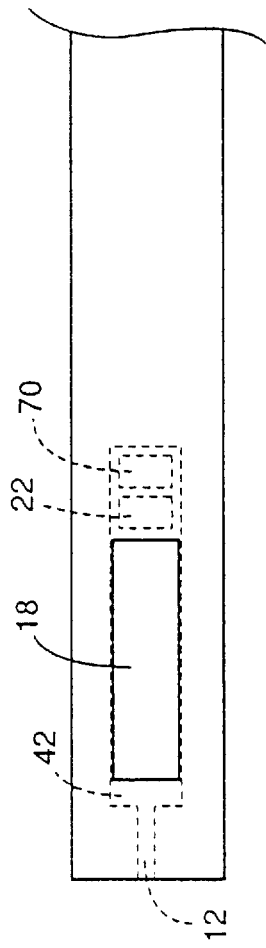
FIG. 5 (A) explanatorily shows a plan view corresponding to FIG. 1(A) of a second embodiment of the NOx sensor according to the present invention, and FIG. 5(B) explanatorily shows a cross-sectional view corresponding to FIG. 1(B).

A second embodiment representatively exemplifies another NOx sensor (second NOx sensor) according to the present invention is shown in FIG. 5(A), (B). The second embodiment adopts a structure similar to that shown in FIG. 2(A) and FIG. 2(B), which is specifically characterized in that the function of the porous material layer 40 in FIG. 2(A), (B) is possessed by a first measuring electrode 70, and a constant current power source is provided on an electromotive force-outputting circuit comprising the first measuring electrode and the first reference electrode of the electrochemical sensor cell in FIG. 2(A), (B) to allow a constant current to flow so that oxygen is pumped out from the first measuring electrode to the first reference electrode, and thus a partial pressure of oxygen in an atmosphere in a porous structure of the first measuring electrode comes to a predetermined value at which NOx is reduced.

Namely, in the second embodiment, the first measuring electrode 70 having the porous structure also functions as both of the second diffusion rate-determining means and the second internal space. At first, the atmosphere of the measurement gas with its partial pressure of oxygen controlled in an internal space 42 is introduced into the inside of the first measuring electrode 70 having the porous structure under a predetermined diffusion resistance.

After that, the oxygen in the atmosphere of the measurement gas introduced into the inside of the first measuring electrode 70 having the porous structure is pumped out from the inside of the first measuring electrode 70 to a reference gas-existing space 10 by the aid of the first reference electrode 30, in a flow amount always corresponding to a previously set current value of the constant current power source, owing to the pumping action effected by the constant current power source 72 provided on the electromotive force-outputting circuit comprising the first measuring electrode 70 and the first reference electrode 30 of the first electrochemical sensor cell. However, the first measuring electrode 70 has the porous structure having the diffusion resistance. Accordingly, pressure loss occurs in the flow of oxygen caused by diffusion effected by the pumping action of the constant current power source 72. The partial pressure of oxygen in the porous structure is lower than that in the internal space 42 by an amount corresponding to the pressure loss.

NOx in the atmosphere diffuses into the first measuring electrode 70 under the predetermined diffusion resistance. NOx is reduced or decomposed, in the vicinity of the surface of the first measuring electrode 70, by the first measuring electrode 70 having the porous structure which also functions as a NOx-reducing catalyst. The partial pressure of oxygen in the atmosphere in the porous structure of the first measuring electrode 70 is increased by oxygen produced by the reduction or decomposition of NOx. When the NOx concentration is zero, the partial pressure of oxygen in the porous structure is lower than that in the internal space 42 by the amount corresponding to the pressure loss. Since the first measuring electrode 70 has the diffusion resistance, the produced oxygen in the first measuring electrode scarcely diffuses into the internal space 42 when the amount of increase in partial pressure of oxygen is smaller than the amount corresponding to the pressure loss as a matter of course, and even when the former is larger than the latter. Therefore, the change in NOx concentration in the measurement gas results in a large change in partial pressure of oxygen in the porous structure.

The constant current power source 72 greatly changes the voltage to be applied to the first electrochemical sensor cell, in order to allow the current of the previously set value to continuously flow through the electromotive force-outputting circuit in response to the change in partial pressure of oxygen in the porous structure of the first measuring electrode 70. The change in voltage, which is applied to the first electrochemical sensor cell by the constant current power source 72 corresponding to the partial pressure of oxygen in the atmosphere in the porous structure, defined by the produced oxygen, is detected by a first potentiometer 32 provided on the electromotive force-outputting circuit of the first electrochemical sensor cell. Accordingly, even a slight amount of produced oxygen can be measured as a large change in voltage. Moreover, the diffusion of produced oxygen into the internal space is suppressed to be less than that of the NOx sensor concerning the first embodiment. Thus the sensitivity for detecting the NOx concentration is more increased than that of the NOx sensor concerning the first embodiment.

Desirably, the partial pressure of oxygen in the internal space 42 is set to be not more than about 1/100 of the NOx concentration in the measurement gas in order to increase the sensitivity for detecting the NOx concentration. If NOx is reduced in the internal space 42 in this procedure, an alloy cermet electrode composed of, for example, Pt/Au is used as the second measuring electrode 22 and the inner pumping electrode 16 in order to lower the ability to reduce NOx.

In the NOx sensor having the structure as described above, the first measuring electrode 70 having the porous structure also functions as the second diffusion rate-determining means and the second internal space. Therefore, it is unnecessary to separately provide a diffusion rate-determining means. Thus the structure of the NOx sensor is simplified, providing an advantage from the viewpoint of cost and applicability to mass production. Moreover, when a diffusion rate-determining means, which is, for example, a diffusion rate-determining layer composed of a porous material layer, is separately provided on the first measuring electrode 70, it is possible to more effectively suppress the diffusion of oxygen produced by the reduction or decomposition of NOx, from the inside of the first measuring electrode 70 to the internal space 42. Thus the sensitivity for detecting the NOx concentration is further improved.

As for the NOx sensor according to the second embodiment, in order to decrease the change in electromotive force of the first electrochemical sensor cell, i.e., the measuring error for the NOx concentration, caused by the change in distribution of oxygen concentration existing in the gas-diffusing direction depending on the oxygen concentration in the measurement gas, it is desirable that the first measuring electrode 70 and the second measuring electrode 22 are arranged in parallel with respect to the direction of diffusion of the atmosphere in the internal space 42, in the same manner as the second embodiment of the first embodiment.

Figure 5B:
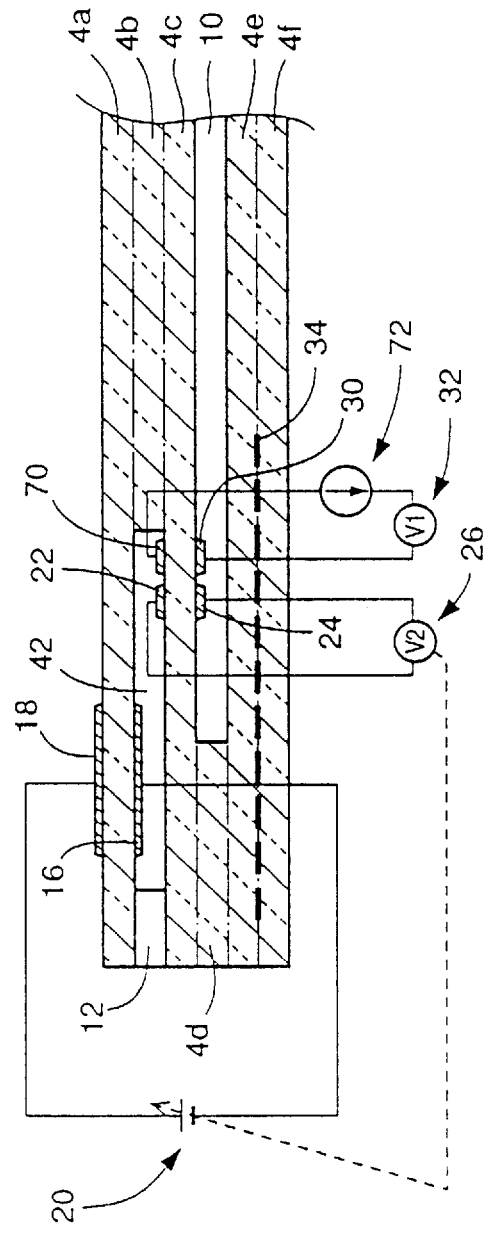

A modified embodiment of the second embodiment, shown in FIG. 6 is different from the second embodiment shown in FIG. 5(A) and FIG. 5(B), which is characterized as follows. Namely, the internal space 42 in FIG. 5(A), (B) is divided into a first internal space 86 communicating with the external measurement gas-existing space through a first diffusion rate-determining passage 12, and a second internal space 88 into which an atmosphere in the first internal space 86 is introduced through a second diffusion rate-determining passage 84 under a predetermined diffusion resistance. The electrochemical pumping cell is located on the first internal space 86, while the first electrochemical sensor cell is located on the second internal space 88. An inner subsidiary pumping electrode 82 is provided in contact with the solid electrolyte layer 4a located on the second internal space 88. The inner subsidiary pumping electrode 82, the solid electrolyte layers 4a, 4b, 4c, and the first reference electrode 30 constitute a subsidiary oxygen-pumping cell for lowering a partial pressure of oxygen in the atmosphere introduced from the first internal space 86 into the second internal space 88 to a degree sufficient to reduce NOx in a porous structure of a first measuring electrode 80 of the first electrochemical sensor cell. The subsidiary oxygen-pumping cell is operated by an external DC power source 90.

Namely, the measurement gas introduced from the first internal space 86 through the second diffusion rate-determining passage 84 undergoes the pumping action effected by the subsidiary oxygen-pumping cell constructed by the inner subsidiary pumping electrode 82 arranged in the second internal space 88, the first reference electrode 30, and the solid electrolyte layers 4a, 4b, 4c. Thus the second internal space 88 is controlled to have a low and constant value of partial pressure of oxygen. The low and constant value of partial pressure of oxygen is stably maintained to be constant even when the oxygen concentration in the measurement gas is high, and hence the change in electromotive force of the first electrochemical sensor cell, i.e., the measuring error for the NOx concentration, caused by the change in distribution of oxygen concentration in the measurement gas depending on the oxygen concentration in the measurement gas, is extremely large. Accordingly, it is possible to further decrease the measuring error for the NOx concentration, caused by the distribution of oxygen concentration in the measurement gas. Moreover, the NOx concentration in the measurement gas can be accurately measured in a state in which the partial pressure of oxygen in the first internal space 86 is previously set to be a predetermined value which is sufficiently higher than that in the second internal space 88. Accordingly, even when inflammable gases such as CO, HC, and $H_2$ are present in the measurement gas in a mixed manner, the inflammable gases can be removed by oxidation in the first internal space 86. Thus it is possible to decrease the measuring error for the NOx concentration, due to interference by the inflammable gases in the second internal space 88, as small as possible. It is needless to say that the subsidiary oxygen-pumping cell can be equivalently applied and installed for the NOx sensor (first NOx sensor) according to the present invention, and thus an equivalent effect can be obtained.

Figure 7:
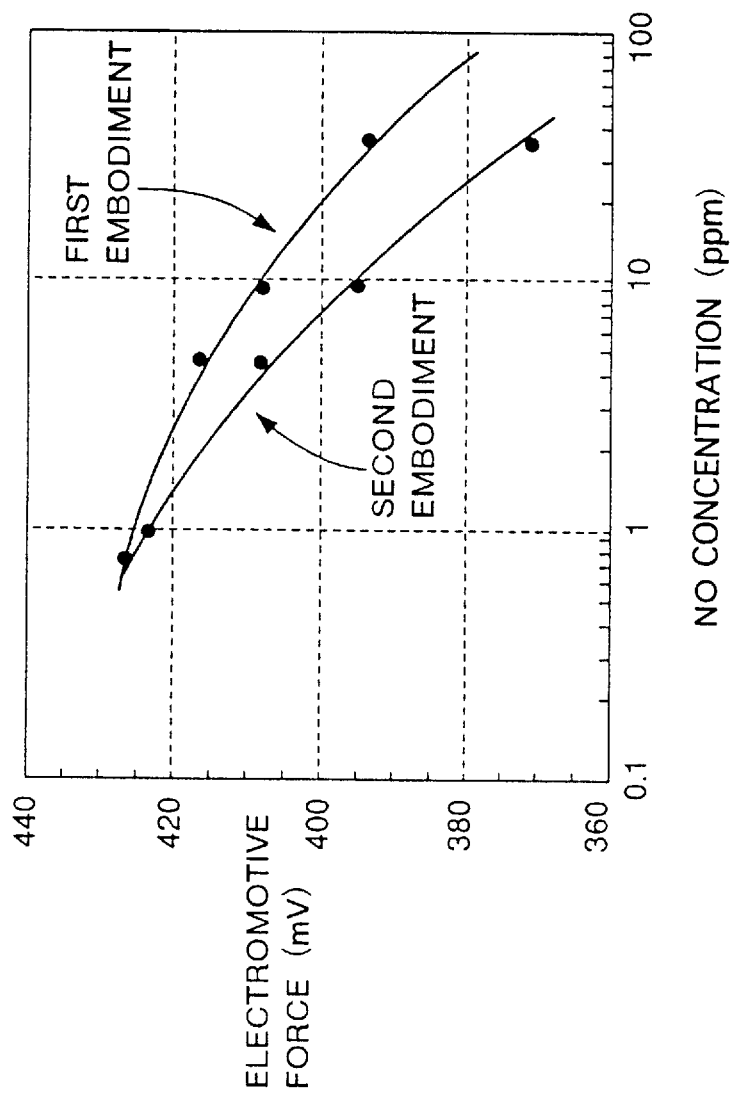
FIG. 7 shows a graph exemplarily illustrating relationships between the NO concentration in a measurement gas and the electromotive force, obtained in the first and second embodiments of the NOx sensor according to the present invention.

The NOx sensors of the first and second embodiments shown in FIG. 1(A), (B) and FIG. 5(A), (B) respectively were used under the following condition. Namely, the pumping voltage of the electrochemical pumping cell was 430 mV. The partial pressure of oxygen in the atmospheres in the first internal space 6 or the internal space 42 was controlled to be $10^{-10}$ atm. In this state, NO as a NOx component in a measurement gas comprising 5% $O_2$ in a carrier gas of $N_2$ was changed in a range of 0.8 to 40 ppm. The change in electromotive force between the first measuring electrode 28 or 70 and the reference electrode 30, obtained under this condition, is shown in FIG. 7. As clarified from the result shown in FIG. 7, the electromotive force changes in a range of about 15 mV in the first embodiment, or in a range of about 30 mV in the second embodiment, in a range of NO concentration of 1 to 10 ppm. Accordingly, a large change in signal can be detected by the first potentiometer 32 even when the NO concentration in the measurement gas is low.

When the NO concentration is determined by measuring the electromotive force as performed by the NOx sensor according to the present invention, it is possible to select the sensitivity to NO and the measuring range by controlling the diffusion resistance concerning the first measuring electrode 28. As for the result shown in FIG. 7, the first embodiment concerns a case of the use of a sum of diffusion resistances of the diffusion rate-determining passage 14 having a cross-sectional area of 0.2 $mm^2$ and the measuring electrode 28 itself comprising a porous cermet having an electrode thickness of 10 μm and a porosity of 40%. The second embodiment concerns a case of the use of only a diffusion resistance of the measuring electrode 70 itself comprising a porous cermet having an electrode thickness of 10 μm and a porosity of 40%. The sensitivity to NO is increased by increasing the diffusion resistance by providing, for example, a porous diffusion rate-determining section such as a porous alumina layer and a porous zirconia layer stacked on the measuring electrode 28, 70. However, it is difficult to perform measurement in a high concentration region. $O_2$ produced by reduction on the electrode is apt to remain in the electrode area, and the oxygen concentration is apt to increase. Therefore, the change in electromotive force becomes large. However, the oxygen concentration in the electrode area is apt to increase due to $O_2$ produced by reduction. For this reason, reduction does not occur if the oxygen concentration exceeds a certain level. Accordingly, it is difficult to perform measurement in a high concentration region. Therefore, the sensitivity and the measuring range should be determined by appropriately setting the diffusion resistance depending on the feature of a region in which the NO concentration is measured.

It is needless to say that the present invention may be carried out in various altered, corrected, and improved forms on the basis of the knowledge of those skilled in the art. It should be understood that any of such forms belongs to the category of the present invention, within a range without deviating from the spirit of the present invention.

As clarified from the foregoing explanation, according to the NOx sensor and the method of measuring NOx concerning the present invention, even when the NOx concentration in a measurement gas is low in a degree of several ppm, an electromotive force is detected, which corresponds to a partial pressure of oxygen in an atmosphere, defined by oxygen produced by reducing or decomposing NOx, in the presence of the diffusion rate-determining means having a predetermined diffusion resistance. Thus a large change in electromotive force, i.e., a large change in signal is obtained as exemplified in FIG. 7 even when the measurement gas component has a low concentration. Moreover, measurement can be performed continuously and accurately with good response over a long period of time.

What is claimed is:

1. A method of measuring a concentration of $NO_x$ as a gas component of a measurement gas, comprising the steps of:

introducing the measurement gas containing the $NO_x$ component from an external measurement-gas space into a first internal space under a first diffusion resistance;

controlling a partial pressure of oxygen in said first internal space to a value at which NO is not substantially decomposed;

introducing the atmosphere from said first internal space into a second internal space under a second diffusion resistance;

deoxidizing or disassociating NO in said second internal space to producing oxygen;

detecting an amount of oxygen by deoxidizing or disassociating NO within said second internal space on the basis of an electromotive force generated due to oxygen concentration at an electrochemical sensor cell arranged in said second internal space; and measuring the concentration of $NO_x$ in the measurement gas by measuring said amount of oxygen.

2. A method of measuring a concentration of $NO_x$ as a gas component of a measurement gas, comprising the steps of:

introducing the measurement gas containing the $NO_x$ component from an external measurement—gas space into a first internal space under a first diffusion resistance;

controlling a partial pressure of oxygen in the measurement gas within said first internal space to a value at which NO is not substantially disassociated;

introducing into a second internal space under a second diffusion resistance the atmosphere from said first internal space;

deoxidizing or disassociating NO in said second internal space to produce oxygen;

detecting an amount of oxygen produced by deoxidizing or disassociating a $NO_x$ component within said second internal space on the basis of an electromotive force generated due to oxygen concentration at an electrochemical cell arranged in said second internal space; and measuring the concentration of $NO_x$ in the measurement gas by said amount of oxygen and the expression $$Cn=(RT/4F)\ln(A/Pno)$$

wherein Cn is the concentration of $NO_x$, F is the Faraday constant, R is the gas constant, T is absolute temperature, A is comparative partial pressure of oxygen or standard partial pressure of oxygen, and Pno is a partial pressure of NO.

3. The method according to claim 2, wherein a partial pressure of oxygen in the atmosphere outside said second internal space is used as said standard partial pressure of oxygen in said electrochemical sensor cell.

4. The method according to claim 2, wherein a partial pressure of oxygen which does not contain oxygen produced by deoxidizing or disassociating NO in said second internal space is used as said comparative partial pressure of oxygen in said electrochemical sensor cell.

* * * * *